United States Patent [19] [11] 4,318,930
Clément et al. [45] Mar. 9, 1982

[54] STRAINS OF YEAST FOR BREAD-MAKING AND NOVEL STRAINS OF YEAST THUS PREPARED

[75] Inventors: Philippe Clément, Roubaix; Annie Loiez née Hennette, Lille, both of France

[73] Assignee: Lesaffre et Cie, Paris, France

[21] Appl. No.: 931,151

[22] Filed: Aug. 4, 1978

Related U.S. Application Data

[63] Continuation-in-part of Ser. No. 863,952, Dec. 23, 1977.

[30] Foreign Application Priority Data

Dec. 24, 1976 [GB] United Kingdom ............... 54172/76

[51] Int. Cl.$^3$ ........................... A23L 1/28; C12N 1/18
[52] U.S. Cl. ..................................... 426/62; 435/172; 435/256
[58] Field of Search ............... 435/172, 255, 256, 260, 435/940, 942; 426/62, 60, 549

[56] References Cited

U.S. PATENT DOCUMENTS 3,930,946 1/1976 Maldonado et al. ............... 435/172
3,954,536 5/1976 Pacchetti et al. .................. 435/172
3,993,783 11/1976 Langejan et al. .................... 435/256
4,172,764 10/1979 Heslot et al. ......................... 435/172

FOREIGN PATENT DOCUMENTS 989247 4/1965 United Kingdom ............... 435/172
1539211 1/1979 United Kingdom ............... 435/172

*Primary Examiner*—Benôit Castel
*Attorney, Agent, or Firm*—Cushman, Darby & Cushman

[57] ABSTRACT

A complete and reproducible process for producing novel strains of yeast, comprises making a first screening test and at least one other screening test selected from a group of screening tests which do not resort to any measurement of gas release, selecting by means of said first and at least one other said screening test the desired strains from a group of diploid strains prepared previously either by hybridation, or by mutation of existing strains. The tests are as follows: A first test consists of measuring the average multiplication coefficient of a given strain by following the optical density variation of a standard medium seeded by a suspension of cells obtained from this strain. A second test consists of measuring in the same manner the average multiplication coefficient of the said strain in the presence of an inhibitor acid added to the standard medium. A third test consists of measuring the maltose adaptation of said strain in the presence of glucose by determining the amount of maltose subsisting in a standard medium after a known amount of glucose added to this medium has been completely consumed. A fourth test consists of measuring the invertase content of said strain. A fifth test consists of measuring the latent time of said strain. The hybridation can consist of systematic haploid crossings derived from quick Saccharomyces Cerevisiae strains adapted to maltose and haploids derived from very slow strains not adapted to maltose, but well adapted to sweet doughs and sometimes also to acid doughs.

4 Claims, No Drawings

STRAINS OF YEAST FOR BREAD-MAKING AND NOVEL STRAINS OF YEAST THUS PREPARED

This is a continuation-in-part of application Ser. No. 863,952 filed on Dec. 23, 1977.

BACKGROUND OF THE INVENTION

1. Field of the Invention

The invention relates to a complete and reproducible process for obtaining new strains of yeasts for bread making. It also relates to the novel strains of yeast thus prepared as well as to fresh or dried yeast for bread making prepared from said new strains.

2. Description of the Prior Art

Quick strains of yeasts are already known which are adapted to maltose—that is to say, enabling the preparation of yeasts which release a large amount of $CO_2$ with doughs constituted by flour and water—and which remain active with doughs of little sweetness, that is to say, not containing more than 5% by weight of sugar with respect to the flour, namely less than 3.3% by weight with respect to the dough.

It is found that these strains exhibit performances which drop appreciably when the sugar content of the dough increases and notably when it exceeds 10% by weight with respect to the flour. Now, such doughs represent a non-negligeable part of bread-making in certain countries.

Moreover, these strains, whose use has been generalised in yeast making for about 10 years, are rapidly inhibited as soon as the dough contains significant concentrations of acetic, sorbic or propionic acids or their salts.

Acid or sour doughs occur in the manufacture of rye bread, leavened bread and others, whose acidity, corresponding to a pH below 4.7, is contributed by a mixture of about 10–50% by weight of acetic acid and about 50 to 90% by weight of lactic acid and which are rarely sweetened, represent also a non-negligeable part of bread making.

Finally, in all countries, there is added to the products of bread making intended to have a long period of preservation or a preservation under difficult conditions, mould-inhibiting agents such as acetic, sorbic, propionic acids and their salts, and this whatever the proportion of sugar contained in the dough. It is known that a bread making yeast resistant to acetic acid, that is to say, whose fermenting power is not inhibited significantly in the presence of undissociated acetic acid, has generally the same property, that is to say, a better resistance, with respect to inhibiting doses of undissociated propionic or sorbic acid.

To overcome the inadequacies of the prior art with regard to bread-making yeast strains, it is an object of the invention to provide a process adapted to permit the obtaining, in simple and reproducible manner, of novel strains of yeast adapted to maltose, characterised by the fact that the yeast, both fresh and dried, of which they enable the preparation and of which certain at least constitute novel industrial products, are:

either still better adapted to maltose, or active with sweetened doughs, that is to say with double containing at least 5% by weight of sugar with respect to the flour, or active with acid doughs, or endowed, preferably, with two of the three above-mentioned properties and preferably with all three.

In order to do this, the specialist in the field has the choice between:

on the one hand, modifying the processes of propagation of yeast, that is to say, its processes of cultivation and, on the other hand, obtaining novel strains by mutation and/or hybridation.

Modification of the cultivation processes is laborious and difficult to put into practice and often magnifies one property more or less to the detriment of another.

Research for novel strains by hybridation and mutation poses complex problems. It is highly uncertain if the objectives and the phenomena in play are not well mastered and if the crossing plans or the mutation process are not clearly defined. It results in any case in the obligation to test thousands even tens of thousands of colonies, which is impossible in practice by means of tests with release of gas under specific conditions (flour, sugar or organic acid mediums), said tests requiring cultivation in a fermenter of some liters as described in Example 1 of French patent application no. 75 20943, the harvesting of this yeast and at least five measurements of gas release according to tests of type A which will be considered below. The problem is complicated by the fact that the results obtained are reproducible with difficulty; for example, a slight modification, difficult to master in the conditions of cultivation can result in considerable variations in respect to the criteria measured.

Nevertheless, research for novel strains is theoretically the best solution, all the more as the employment of specific cultivation conditions can only improve, reinforce the natural properties possessed by the hybrids or mutants.

The two routes of research are in fact complementary and not concurrent.

GENERAL DESCRIPTION OF THE INVENTION

The process according to the invention is characterised in that by means of the first and of at least one other screening test selected from a group of screening tests not calling upon any measurement of gaseous release, the desired strains are selected from a group of diploid strains previously prepared either by hybridation, or by mutation of the existing strains, the tests of said group of tests being constituted by:

a first test consisting of measuring the mean or average multiplication coefficient of a given strain by following the variation of the optical density of a standard medium seeded by a suspension of cells obtained from this strain, a second test consisting of measuring in the same manner the mean multiplication coefficient of said strain in the presence of an inhibitor acid added to the standard medium, a third test consisting of measuring the maltose adaptation of said strain in the presence of glucose by the determination of the amount of maltose subsisting in a standard medium after a known amount of glucose added to this medium has been completely consumed, a fourth test consisting of measuring the invertase content of said strain, the invertase unit being defined as production of a micromole of reducing sugars in five minutes per mg of yeast dry matter at 30° C. and at pH 4.7, without plasmolysis of the yeast, namely a demi-micromole of invert saccharose, a fifth test consisting of measuring the latent time of said strain, that is to say the delay in the starting of multiplication, by following the variation in the optical density of the yeast suspension applied in the first test after having conferred on this suspension a sugar concentration of at least 20%.

In the abovesaid process, for the first test, it is possible to produce a preculture of 48 hours at 30° C. in a test tube containing 10 ml of a medium having the following composition:

| yeast extract | 1% |
|---|---|
| peptone | 2% |
| saccharose | 2% | denoted in the following description by the name "YEP medium".

The preculture can also be made in other media.

A known amount of this preculture serves then for seeding an optical flask containing 30 ml of a medium identical with or equivalent to the YEP medium. The growth curve of the yeast is then established by measurement of the optical density every hour at 600 mµ.

From this curve, it is possible to calculate the mean multiplication coefficient $\mu$ given by:

$$\mu = \frac{1}{x}\frac{dx}{dt}$$

where x represents the cellular population at the time t.

This first test has a double advantage in the sense that it can serve as a control for the other tests and that it permits the elimination of all the diploid strains not having a sufficient multiplication coefficient, that is to say, capable of giving in sufficient yield or of having too low a gaseous release, as for example strains which have been treated too severely during a mutation treatment.

Again in the above-mentioned process, for the second test, the inhibitor acid added to the cultivation medium consists of acetic acid or of a mixture of acetic acid and lactic acid in an amount and in proportions such that it inhibits to a ratio comprised between 50% and 90% the growth of a control strain showing on dough containing inhibiting organic acids and/or on sweetened dough, a considerable reduction in its power of $CO_2$ release.

It has, in fact, been found that there existed a non-negligeable probability that the strains which, in a medium containing an amount of acetic acid inhibiting in a large proportion the growth of known quick yeast hybrids adapted to maltose, show a better growth than these hybrids and, exhibit a least fermentation inhibition with acid doughs (more than 50% of chances), or, and are more active and often distinctly more active with sweetened doughs than said quick hybrids, adapted to maltose.

Again in the abovementioned process for the third test, the yeast strain is placed in the presence of a sugar solution containing a known amount of glucose and of maltose. The amount of glucose is selected so that it is entirely consumed at the end of the test which lasts generally one hour. At the end of the test, the reaction is stopped by cold centrifugation and the sugar remaining in the supernatent liquid is determined. The percentage of maltose consumed by the yeast is deduced therefrom. It was found that the percentage of maltose consumed generally well manifested the more or less good adaptation of the tested strain to the fermentation of maltose and also the speed of the strain.

A modification consists of following as a function of time the disappearance of the glucose and of the maltose added together. The disappearance of the total sugars is followed by determination with anthrone and that of the glucose by specific enzymatic determination, the amount of maltose being determined by difference.

It was observed that the strains not adapted to maltose did not ferment, in this test, the maltose as long as glucose remained; on the other hand, the strains adapted to maltose ferment more or less rapidly the maltose even when there is still glucose.

The abovesaid test is carried out by starting with a known amount of dry material obtained from the yeast strain tested. This known amount of dry yeast material can for example be obtained by filtration of the yeast present in the optical flask at the end of the first test, or by filtration of an amount of yeast obtained within the scope of a similar shaken culture and by determination of the dry material in this cake, which dry material is generally of the order of 20%.

The adaptation to the maltose can also be estimated semi-quantitatively by recovering colonies of tested strains spaced regularly on a petri dish by a filter paper soaked in a maltose solution, for example 0.1 Molar and in Bromo-Cresol Purple acidity type indicator dye and by monitoring the colorimetric change at the end of a given time. This coarse test is a first possible approach, essentially after mutation. In any case, the methods described above must always be employed to refine this first possible selection.

Again in the above mentioned process there is indicated, in connection with the fourth test, that the invertase unit may be determined for example in the following manner. It starts with a known amount of dry yeast material of the order of 0.1 to 0.4 mg which can be obtained by filtration of the yeast present in the optical flask at the end of the first test. This amount of dry yeast material is placed in the presence of saccharose at a final 0.1 Molar concentration in a test tube in a buffered medium, buffer acetate at pH 4.7 placed in a water bath at 30° C. At the end of five minutes, the inversion reaction of the saccharose is blocked by the addition of a reactant sodium dinitrosalycilate which serves to determine the reducing sugars formed, by colorimetric reaction.

The greater or lesser richness in invertase can also be evaluated semi-quantitatively by colonies of strains tested on a petri dish, by covering the dish with a filter paper soaked in saccharose and the necessary reactant for the enzymatic determination of the glucose formed, by colorimetric reaction (0 - dianisidine, for example). This test is a first possible approach, essentially after mutation. It can, in some cases, permit a first very rough selection. In any case, the simple and practical method described above must always be employed to refine this first selection.

It has been found that a strong probability exists that all strains of yeast having less than 35 invertase units, preferably less than 30 units and, more preferably still, less than 20 invertase units, are active on sweetened doughs especially if they have given good results in the first test and in the third test.

By way of indication it is to be recalled that the hybrids of quick yeast adapted to maltose, employed until now in yeast making, have an invertase content which is always greater than 40.

Again, in the above mentioned process, it is pointed out, with respect to the fifth test, that the shorter the latent time, the more likely the tested strain is to be osmotolerant, that is to say, active with sweetened doughs.

In conclusion, it is emphasized that the conjugate use of the first and third tests can either permit the selection of strains which are even quicker and better adapted to maltose than those which have been used hitherto, or permit the selection, when it is coupled with at least one of the other tests described, of strains adapted to maltose and more active with sweetened doughs or, preferably, with acid doughs.

Thus, it has been found that a selection effected by using in conjugated manner, the first screening test (the criterion taken being that any strain selected should have a multiplication coefficient equivalent to that of the best commercial baker's yeast), the third test (the criterion taken being that any strain selected should have an adaptation to maltose corresponding to an amount of maltose consumed equal to at least 50% of the maltose consumed in the operational method taken with the best strains of commercial yeast adapted to maltose) and the fourth test (the criterion taken being that any strain selected should have an invertase content less than 35 units, preferably less than 30 units, and more preferably still, less than 20 units), leads to strains better adapted to maltose and/or more active with sweetened doughs.

All the strains thus selected have novel characteristics with respect to all previously known strains.

It has also been found that a selection effected by using in conjugated manner the first screening test (the criterion taken being that any strain selected should have a multiplication coefficient equivalent to that of the best strains of commercial baker's yeasts), the third test, (the criterion taken being that any strain selected should have an adaptation to maltose corresponding to an amount of maltose consumed equal to at least 50% of the maltose consumed by the best strains adapted to maltose) and the second test (criterion taken being that any strain selected should have less inhibition of the culture in the presence of acetic acid added to the standard medium), leads to strains better adapted to maltose and/or more active with acid doughs and/or often equally more active also with sweetened doughs.

All the strains thus selected have novel characteristics with respect to all previously known strains.

A selection effected by means of a combination of the four first tests described above leads to strains having at least two and mostly three of the following properties:
improved adaptation of maltose,
better activity with sweetened doughs having from 1 to 20% of sugar,
better activity with doughs containing undissociated acetic acid.

All the strains thus selected have novel characteristics with respect to all previously known strains.

The fifth test (the selection criterion taken being the search for as short as possible a latent time when there is added to the standard medium of the first test an amount corresponding to a concentration of saccharose in the medium of 30%) can serve to confirm the significance of the results of the fourth test (low invertase content). It can also serve, associated with the first test, and preferably also with the fourth test (the selection criterion taken being an invertase content less than 20 units) for seeking strains particularly active with doughs with 10-25% of saccharose.

Accordingly and still in the above mentioned process, the hybridation according to the invention consists essentially of systematic crossings of haploids derived from strains of quick saccharomyces cerevisiae adapted to maltose and haploids derived from very slow strains, not adapted to maltose, but well adapted to sweetened doughs and sometimes also to acid doughs belonging to the Saccharomyces genus, and notably to the Saccharomyces cerevisiae species.

As indicated above, these strains of quick saccharomyces cerevisiae baker's yeasts adapted to maltose, are well known and are generally those which serve at present for the manufacture of fresh yeast marketed throughout the world. Such yeast are for example described in British Pat. Nos. 868 621 (strain ATCC 13 601), 868633 (strain ATCC 13 602), 989247 (strains CBS Ng 740 and Ng 1777), etc. This list of patents and of strains deposited at the collection centres such as ATCC (American Type Culture Collection), the CBS (Centraalbureau voor Schimmel Cultures de Baarn) or NCYC (National Collection of Yeast Cultures Agricultural Research Council's Food Research Institute Colney Lane Norwich, Norfolk NR4 7UA ENGLAND) is not limiting nor complete.

Slow yeast-making strains Saccharomyces Cerevisiae, other strains of Saccharomyces with an osmophile character, like for example strains of Saccharomyces rosei, Saccharomyces rouxii, are available at the principal collection centres such as the ATCC, CBS or the NCYC.

It has been found that certain slow yeast-making strains, used at other times in Europe, and certain distillery strains, like for example the isolate which is deposited at the NCYC under no. R30 and which is described in French Pat. No. 75 20943, were extremely interesting materials for this crossing operation.

Sporulation of the starting strains, the obtaining of the haploids, and the conjugation of these haploids are carried out according to the techniques described in Chapter 7 of "Sporulation and Hybridization of Yeasts" by R. R. FOWELL in the book "The Yeasts", volume 1, edited by Anthony H. ROSE and J. S. HARRISON, 1969, Academic Press, London and New York. The hybridation technique adopted between haploids of Saccharomyces Cerevisiae was the mass-mating technique. Micro-manipulation may be the preferred method for crossings in which haploids of other Saccharomyces than Saccharomyces Cerevisiae take part.

In this way the strains are obtained which meet the criteria taken in the first and third tests, as well as the criteria taken in one or several of the three other tests.

It has been verified that the large majority of yeasts obtained from strains selected by means of the group of tests of the process according to the invention had at different successive stages of cultivation, namely at the three liter cultivation stages, and then cultivation in a pilot fermenter, the calculated fermentative properties, these properties being measured by means of tests A (carried out by means of the BURROWS and HARRISON fermentometer) and tests B (carried out by means of the CHOPIN zymotachygraph) which are described below.

Again in the above mentioned process, the mutation according to the invention which constitutes a completely novel route for producing industrial strains of bread-making yeast, which route it has been possible to take due to the group of tests of the same process, consists essentially of a mutagenesis carried out on the haploid or on the diploid and applying mutagenic agents such as ethylmethane sulfonate and N-methyl, N-nitro, N-nitrosoguanidine or NTG, the haploids obtained at the end of the mutagenic treatment being then utilisable as crossing material in the hybridation operations.

Preferably, recourse is had to mutagenesis with NTG resulting in a survival rate comprised between 2% and 80%.

The survival rate selected must be higher operating with haploids than when operating with diploids so that these haploids retain their aptitude to be conjugated. The survival rates generally selected for working with haploids have been comprised between 40% and 80%.

This being the case, the novel quick strains, adapted to maltose, obtained by the application of the process according to the invention, may be characterized by the fact that they enable the preparation of both fresh and dried yeast, themselves characterized by their release of gas that they give within the scope of a certain number of tests denoted by the references A ($A_1$, $A'_1$, $A_2$, $A'_2$, $A_3$, $A'_3$, $A_4$, $A'_4$, $A_5$, $A'_5$) carried out by means of the BURROWS and HARRISON fermentometer and by the references B ($B_1$, $B'_1$ and $B'_3$) carried out by means of the CHOPIN zymotachygraph and which will be defined below.

TEST $A_1$ (FRESH COMPRESSED YEAST)

To 20 g of flour incubated at 30° C., is added a weight of compressed yeast corresponding to 160 mg of dry material, this yeast being diluted in 15 ml of water containing 27 g of NaCl per liter and 4 g $(NH_4)_2 SO_4$ per liter; it is kneaded by means of a spatula for 40 seconds, so as to obtain a dough which is placed on a waterbath regulated to 30° C.; 13 minutes after the beginning of kneading, the vessel containing the dough is hermetically closed; the total amount of gas produced is measured after 60, and then 120 minutes; this amount is expressed in ml at 30° C. and under 760 mm of Hg,

TEST $A'_1$ (DRY YEAST)

Identical with test $A_1$, but prior to kneading, the dry yeast is rehydrated in distilled water, at 38° C.; for this purpose 40% of the volume of water of hydration applied is used; the complement of water, supplemented with 405 mg of NaCl, is added at the end of the 15 minutes of rehydration,

TEST $A_2$ (FRESH COMPRESSED YEAST)

Test identical with test $A_1$, but there is added to the flour 100 mg of saccharose; the total amount of gas produced is measured after 60 minutes,

TEST $A'_2$ (DRY YEAST)

Test identical with test $A'_1$, but there is added to the flour 100 mg of saccharose; the total amount of gas produced is measured after 60 minutes,

TEST $A_3$ (FRESH COMPRESSED YEAST)

Test identical with test $A_1$, but there is added to the flour 2 g of saccharose; the total amount of gas produced is measured after 60 minutes,

TEST $A'_3$ (DRY YEAST)

Test identical with test $A'_1$, but there is added to the flour 2 g of saccharose; the total amount of gas produced is measured after 60 minutes.

TEST $A_4$ (FRESH COMPRESSED YEAST)

Test identical with test $A_1$, but to the flour is added 5.5 g of saccharose; the total amount of gas produced is measured after 60 minutes,

TEST $A'_4$ (DRY YEAST)

Test identical with test $A'_1$, but to the flour is added 5.5 g of saccharose; the total amount of gas produced is measured after 60 minutes,

TESTS $A_5$ AND $A'_5$

Tests identical respectively with tests $A_1$ and $A'_1$, with the difference that there is added to the yeast suspension, just before the addition of the latter to the flour, an amount of 0.15 ml of a mixture constituted by 15 g of acetic acid and 80 g of lactic acid, these 0.15 ml being substituted for 0.15 ml of dilution water,

TEST $B_1$ (FRESH COMPRESSED YEAST AND INSTANT DRY YEASTS NOT NEEDING PRIOR REHYDRATION)

To 250 g of flour, is added a weight of compressed yeast or instant dry yeast corresponding to 1.6 g of yeast dry material, and 150 ml of salted water (50 g of salt/1.51 of water); it is kneaded for 6 minutes; the temperature of the dough must be 27° C. at the end of kneading; the dough is placed in the apparatus and 6 minutes, measured exactly, after the end of kneading the chamber thermostatted to 27° C. is placed under pressure; the total release recorded on the graph, in ml, is measured after 1 hour and 3 hours,

TEST $B'_1$ (DRY YEASTS REQUIRING REHYDRATION)

Tests identical with Test $B_1$ but prior to kneading, the dry yeast is rehydrated in distilled water at 38° C. (50 ml) for 15 minutes; the complement of water and of salt is added at the end of the 15 minutes of rehydration,

TEST $B'_3$

Test identical with test $B'_1$, with the difference that there is added to the yeast suspension obtained after dilution of the fresh yeast or after rehydration of the dry yeast, just before kneading, an amount of 2 ml of a mixture constituted by 15 g of acetic acid and 80 g of lactic acid, these 2 ml substituted for 2 ml of diluting water.

The novel strains obtained can hence be characterised by the commercial yeasts whose production they permit and which will be defined below.

1. Strains giving fresh yeasts active with sweetened doughs and characterised by the fact that they give rise to:

a gas release equal to or greater than 112 and, preferably, to 115 ml of $CO_2$ in test $A_1$ in 2 hours, a gas release equal to or greater than 1500 ml of $CO_2$ in test $B_1$ in three hours and, preferably, equal to or greater than 135 ml of $CO_2$ in test $A_1$ and 1700 ml in test $B_1$, a gas release equal to or greater than 53, preferably to 55 ml of $CO_2$ in 1 hour in test $A_2$ and, more preferably again, equal to or greater than 60 ml in this test in 1 hour, a gas release equal to or greater than 50 ml of $CO_2$ in 1 hour in test $A_3$ and, preferably, equal to or greater than 55 ml in test $A_3$ in 1 hour, a gas release equal to or greater than 25 ml of $CO_2$ in test $A_4$ and, preferably, equal to or greater than 30 ml of $CO_2$ in 1 hour and more preferably again, equal to or greater than 35 ml of $CO_2$, the yeast reaching the preferred values for two of the abovesaid tests being particularly preferred.

2. Strains giving dry yeast active with sweetened doughs and characterised by the fact that they give rise to:

a gas release equal to or greater than 98, preferably to 100 ml of $CO_2$ in test $A'_1$ in 2 hours, greater than or equal to 1350 $CO_2$ in test $B_1$ in 3 hours and, preferably, equal to or greater than 115 of $CO_2$ in test $A'_1$ and to 1500 ml of $CO_2$ in test $B_1$ in 3 hours, a gas release equal to or greater than 46, preferably to 48 ml of $CO_2$ in test $A'_2$ in 1 hour, and, preferably, equal to or greater than 52 ml in test $A'_2$, a gas release equal to or greater than 44 ml of $CO_2$ in test $A'_3$ and, preferably, equal to or greater than 47 ml of $CO_2$ in test $A'_3$, a gas release equal to or greater than 21 ml of $CO_2$ in test $A'_4$ and, preferably, equal to or greater than 26 ml of $CO_2$.

3. Strains giving fresh yeast active with acid doughs and characterised by the fact that they give rise to:

gas release equal to or greater than 115 ml of $CO_2$ in test $A_1$ in 2 hours and equal to or greater than 1500 ml of $CO_2$ in test $B_1$ in 3 hours and, preferably, equal to or greater than 135 ml of $CO_2$ in test $A_1$ and to 1700 ml of $CO_2$ in test $B_1$, a gas release equal to or greater than 40 ml of $CO_2$ in test $A_5$ in 1 hour and, preferably, equal to or greater than 45 ml of $CO_2$ in test $A_5$ in 1 hour, a gas release equal to or greater than 900 ml of $CO_2$ in test $B'_3$ in three hours and, preferably, equal to or greater than 1000 ml of $CO_2$ in this test $B'_3$ in 3 hours.

4. Strains giving dry yeasts active with acid doughs and characterised by the fact that they give rise to:

a gas release equal to or greater than 100 ml of $CO_2$ in test $A'_1$ in 2 hours, greater than 1350 ml of $CO_2$ in test $B_1$ in 3 hours and, preferably, equal to or greater than 115 of $CO_2$ in test $A'_1$ and to 1500 ml in test $B_1$ in three hours, a gas release greater than or equal to 32 ml of $CO_2$ in test $A'_5$ in 1 hour and, preferably, equal to or greater than 38 ml of $CO_2$ in test $A'_5$; a gas release equal to or greater than 750 ml of $CO_2$ in test $B'_3$ in 3 hours and, preferably, equal to or greater than 820 ml of $CO_2$ in test $B'_3$.

5. Strains giving fresh yeast, on the one hand, and dry yeast, on the other hand, active with sweetened doughs and with acid doughs and characterised by the fact that the first give rise simultaneously to gas releases shown by the abovementioned fresh yeast, active with sweetened doughs and by the abovesaid fresh yeasts active with acid doughs and the second give rise simultaneously to the releases shown by the abovesaid dry yeasts active with sweetened doughs and by the abovesaid dry yeasts active with acid doughs.

In the foregoing, there has generally been denoted by fresh yeasts, those which have a content of dry material of about 28 to 35% and by dry yeasts those which have a content of dry material higher than 92%.

The nitrogen content of these yeasts has generally been selected within the following ranges:
about 7.5 to 8.5 for fresh compressed yeast,
about 7.2 to about 8.2 for dry yeast.

Once the strain sought is available, it is possible to prepare the fresh compressed yeast corresponding, having a content of dry matter in the neighborhood of 28 to 35% by resorting to a conventional propagation scheme adapted to provide fresh yeast stable in preservation and stable on drying. These yeasts can then be dried to about 92% of dry material or more by means of a particularly gentle drying process.

Preferably, the cultivation of the yeast is conducted so as to obtain a fresh yeast with 28–35% of dried matter having the following characteristics:

an amount of budding below 5% and, preferably, less than 1%, cryoscopic lowering of the water external to the yeast below 0.5° C. and, preferably, below 0.3°. It is pointed out that, to measure the cryoscopic lowering of the external water of a fresh compressed yeast, a cream is produced with 100 g of the pressed yeast and 30 g of completely demineralised water, this cream is centrifuged and cryoscopic lowering of the supernatant liquid obtained is measured, for example, by means of a BECKMAN type cryoscope (PROLABO no. 0329 600). The lowering of the freezing point measured is proportional to the amount of gram-molecules of dissolved substances in the external water.

If it is desired to obtain very quick yeast, fairly high nitrogen contents are selected: 8–8.5% of nitrogen to dry matter, even a little more. If it is desired to obtain yeast having more particular characteristics as for example, stability to drying, the following characteristics are rather to be sought:

protein content corresponding to the optimum of the strain cultivated taking into account the desired characteristics; this content varies according to the strains and the desired characteristics for the yeast but for relatively quick strains it is of the order of 7.5% to 8% of nitrogen to dry matter or even less; the optimum of the nitrogen content for stability to drying may be defined as being the value above which any increase in this content no longer gives more than a slight gain in activity but, after drying, an additional loss in activity equal to or greater than this gain. This optimum depends much on the strain, on the conditions of culture, on a reference test (with sugar, without sugar). It can only be determined experimentally case by case. It is of course obvious to the specialist that all the values of nitrogen to dry matter given above are only indicative;

$$\frac{trehalose}{dry\ material} \geq 12\%;\ 2.3 \leq \frac{N}{P_2O_5} \leq 3.8$$

Preferably, it will be particularly sought to provide the culture medium with the growth factors of which each strain has a need: biotin, group B vitamins etc.

To the yeast intended for drying, is preferably added a fine emulsion constituted by a suitable emulsifier, such as, for example, sorbitol esters, polyglycerol esters in the proportion of 1.5 to 2% of dry yeast matter and if necessary a thickening agent.

Yeast intended for drying, of 30–35% dry matter, is extruded through a grid of mesh width 0.5 to 3 mm, and, preferably, 0.5 to 1 mm.

It is then dried to about 92% of dry matter or more, preferably to a content of dry matter comprised between 94 and 97% by a particularly gentle drying. This can be a fast pneumatic drying, a fluidised bed drying or a combination of these two methods of drying. Preferably, the drying will be conducted so that the temperature of the yeast does not exceed 30° C. at the beginning of the drying and 40° C. at the end of drying.

To enable the invention to be better understood, there are described below, be means of some examples, the production of some strains of yeast according to the invention, the preparation of fresh yeasts and dry yeasts from these strains and the properties of the fresh yeasts and dry yeasts thus obtained.

DESCRIPTION OF PREFERRED EMBODIMENTS

EXAMPLE 1

Two quick strains, adapted to maltose, stable to drying, deposited by applicants at the N.C.Y.C. under nos. N.C.Y.C. 875 and N.C.Y.C. 876, were sporulated.

Two slow strains, very osmotolerant, that is to say, very active with sweetened doughs, deposited by applicants at the N.C.Y.C. under nos. R30 and N.C.Y.C. 877, were sporulated.

For each group of strains, ten haploids of mating type a and ten haploids of mating type α, were isolated. By mass-mating, each haploid of one group was then conjugated with all the haploids of the opposite mating type of the other group. In this way 196 hybrids were obtained.

These 196 hybrids were tested with the first, the second, and the third screening tests and the fourth screening test.

The growth curves of the first and second tests were effected in optical flasks, flasks provided with a calibrated tube enabling colorimetric reading without sampling of the medium. The YEP culture medium was composed of 1% yeast extract, 2% of peptone and 2% saccharose and it was seeded with 0.3 to 0.5 ml of a stirred pre-culture of the hybrid to be tested in a liquid medium with 1% of sugar.

The second test was practiced by adding to the culture medium of the first test a glacial acetic acid in the proportion of 0.13 and 0.14 ml, namely 0.433% and 0.466%.

The third and the fourth test were carried out on the yeast harvested by centrifugation or filtration of the culture practised in the scope of the first test. The yeast harvested was washed to remove the amount of sugar from the culture medium, which sugar could falsify the results of the third test.

The third test was carried out in an 0.01 M phosphate buffer medium, pH 6.5, the reaction mixture comprising:

| | |
|---|---|
| Yeast | 20 to 25 mg of dry matter |
| Glucose | 4 mg |
| Maltose | 2 mg. |

The reaction is carried out at 30° C. for one hour and it is arrested by sudden cooling and cold centrifugation.

The determination of the supernatant sugar is done by the anthrone colorimetric method.

The fourth test is practised on 0.1 to 0.4 mg of dry yeast matter which are placed in the presence of saccharose at a final concentration of 0.1 Molar, in a test tube in a buffered medium with acetate buffer at pH 4.7, placed in a water bath at 30° C. At the end of 5 minutes, the saccharose inversion reaction is blocked by the addition of the reactant with sodium dinitrosalicylate which serves to determine reducing sugars formed, by colorimetric reaction.

Within the scope of the first screening test, can be determined the coefficient $\mu$: increase in population per unit time and per unit mass of population for quick commercial yeast strains or starting strains, the control value found being denoted by $\mu_t$.

Within the scope of the first test, there are eliminated all hybrids for which:

$$\mu < 0.9\ \mu_t.$$

Within the scope of the second test, it is observed that all the quick strains, adapted to maltose employed have a:

$\mu$ in 0.433% acetic acid $< 0.4\ \mu_t$ and a
$\mu$ in 0.466% acetic acid $< 0.25\ \mu_t$ but that a slow strain, very osmotolerant and rather insensitive to acetic acid like the strain N.C.Y.C. R30, has a $\mu$ in 0.433% acetic acid $> 0.6\ \mu_t$ and a
$\mu$ in 0.466% acetic acid $> 0.4\ \mu_t$.

Within the scope of this second test, will be considered as kept for subsequent examination are all strains giving:

$\mu$ in 0.433% acetic acid $> 0.55\ \mu_t$ and a
$\mu$ in 0.466% acetic acid $> 0.32\ \mu_t$.

Within the scope of the third test, it is observed that quick strains considered as adapted to maltose, consume 60–80% of the maltose present, but that, on the other hand, a slow strain like N.C.Y.C. R.30 consumes less than 20% of the maltose present. Within the scope of this test, there are eliminated all strains consuming less than 35% of the maltose present and the strains consuming more than 60% of the maltose are retained. The strains consuming between 35% and 60% of the maltose present are only retained if they have been retained according to the criteria of the second test or according to the criteria of the fourth test.

In the fourth test, all the strains are kept which titrate less than 35 invertase units and, preferably, less than 30 invertase units and, more preferably, less than 20 invertase units.

Within the scope of the selection as described above, 10 hybrids of the 196 obtained by crossing were kept.

It is remarkable that the hybrids selected having the following properties:
  growth curve equivalent to the controls in the first test,
  adaptation to maltose characterised by a consumption of at least 35% of the maltose present in the second test, that is to say at least 50% of the maltose consumed by the control quick strains adapted to maltose,
  invertase content less than 35 units and, preferably, less than 30 units and, more preferably, less than 20 units in the fourth test, or/preferably and growth in the presence of acetic acid characterised by a:
  $\mu$ in 0.433% of acetic acid $> 0.55\ \mu_t$ and/or a $\mu$ in 0.466% of acetic acid $>0.32$ $\mu_t$, that is to say lesser inhibition in the presence of acetic acid than the control quick strains adapted to maltose, are novel strains for the production of yeast for breadmaking, no strain used in the breadmaking yeast industry combining these three or four characteristics.

These ten selected hybrids are then tested by conventional means:

cultivation in fermenters of three liters such as described in Yeast Technology, J. White (1954) pages 103 to 106 where the culture medium has a total volume of 1100 ml, the sugar is added in the form of molasses, the air is filtered through a diaphragm of the Millipore type at the rate of 1 m³/hour and seeding is carried out by 300 mg of yeast obtained by anerobic cultivation in flasks, culture aerated and stirred on a battery of the New Brunswick Scientific Company of 5 liters, of useful volume 3/3.5 liters, then drying the yeast harvested, or culture in a battery of pilot fermenters of 80 liters useful volume such as described in Example 2 of French Pat. No. 75 20943, then drying.

The cultures at the stage of the WHITE type 3 liter fermenter established that 5 of the 10 hybrids selected have most interesting novel characters. In Table 1 are given the results obtained in the same series of experiments for these 5 hybrids, several hybrids of quick yeast adapted to maltose, taken as controls, and a slow strain, namely N.C.Y.C. R30 which is particularly active.

TABLE 1

| Strains used | Invertase units | Test A₁ 1 hour | Test A₂ | Test A₃ | Test A₄ |
|---|---|---|---|---|---|
| Controls (hybrids of quick yeast adapted to maltose) | 45 to 140 | 57 | 64 | 46 | 8 to 16 |
| N.C.Y.C.R30 | 25 | 29 | 46 | 56 | 26 |
| Hybrid 1 | 23 | 52 | 61 | 55 | 24 |
| Hybrid 2 | 37 | 58 | 68 | 51 | 17 |
| Hybrid 3 | 35 | 65 | 72 | 56 | 18 |
| Hybrid 4 | 32 | 56 | 67 | 62 | 23 |
| Hybrid 5 | 29 | 52 | 62 | 60 | 25 |

After tests in batteries of fermenters of greater volume and after tests in factories, it was hybrids 3 and 5 which were kept and filed at N.C.Y.C.

Hybrid no. 3 received the no. N.C.Y.C. 848 and hybrid no. 5 received no. N.C.Y.C. 847.

In Table 2 are given the results obtained by these two hybrids in the factory after culture of 100 m³ leading to a harvest of about 25 tons of fresh yeast, conducted so as to obtain:

a nitrogen content in the dry material of about 8%, a $P_2O_5$ content in the dry material of about 2.3%, a trehalose content in the dry material of about 13%, a ratio of buds of the order of 1%, a cryoscopic lowering of the external water of the yeast of the order of 0.3° C.

By way of comparison there are given the results obtained with a hybrid yeast adapted to maltose and the N.C.Y.C. R30 (table II as regards fresh yeast and table III are regards the dry yeast).

TABLE II

| | FRESH YEASTS | | | | | | | | |
|---|---|---|---|---|---|---|---|---|---|
| | | | | | | B₁ | | B₃' | |
| Strain | A₁ | A₂ | A₃ | A₄ | A₅ | 1 h | 3 h | 1 h | 3 h |
| Quick yeast hybrid adapted to maltose | 55 + 80 = 135 | 59 | 49 | 22 | 28 | 350 | 1700 | 60 | 400 |
| NCYC R 30 | 37 + 48 = 85 | 52 | 56 | 40 | 33 | 260 | 1200 | 120 | 650 |
| NCYC 848 | 60 + 80 = 140 | 64 | 53 | 33 | 53 | 420 | 1780 | 200 | 1160 |
| NCYC 847 | 55 + 75 = 130 | 63 | 57 | 37 | 50 | 400 | 1700 | 250 | 1200 |

TABLE III

| | DRY YEASTS | | | | | | | | |
|---|---|---|---|---|---|---|---|---|---|
| | | | | | | B₁ | | B₃' | |
| Strain | A₁' | A₂' | A₃' | A₄' | A₅' | 1 h | 3 h | 1 h | 3 h |
| Quick yeast hybrid adapted to maltose | 48 + 70 = 118 | 50 | 41 | 18 | 24 | 300 | 1500 | 45 | 300 |
| NCYC R30 | 32 + 43 = 75 | 45 | 47 | 32 | 29.5 | 230 | 1050 | 90 | 500 |
| NCYC 848 | 51 + 68 = 119 | 53 | 45 | 25 | 43 | 350 | 1550 | 120 | 830 |
| NCYC 847 | 46 + 61 = 107 | 53 | 48 | 28 | 38 | 300 | 1470 | 110 | 830 |

The principal taxonomic characteristics of the strains of *Saccharomyces Cerevisiae* N.C.Y.C. 847 and N.C.Y.C. 848 are shown in Table VI.

EXAMPLE 2

To try to obtain strains with a low invertase content, the haploids of slow strains obtained within the scope of Example 1 which seemed most interesting, were crossed with haploids of quick strains adapted to maltose which had undergone a mutation treatment intended to lower their invertase content. The mutagenic treatment was conducted in the following manner:

the haploid strainderived from a fresh preculture was reinjected into the culture medium and brought to the exponential phase of growth. The yeast was harvested sterilely by centrifugation and resuspended in Tris buffer of pH 6.6. The final concentration of cells was $10^7$ to $10^8$ cells per ml. The nitrosoguanidine mutagenic agent was added to a final concentration of 200 to 400 micrograms/ml.

The reaction was carried out at 30° C. for a period of 15 to 60 minutes. At the end of the reaction, after dilution with a large amount of salt water, it was centrifuged cold. The treated haploid cells were then brought to a suitable dilution and spread over a gelose medium in a petri dish. According to the treated haploid strain, survival rates of 10 to 80% were obtained.

The haploids treated in the treatment which gave a survival rate higher than 40% were retained for screening.

As the screening test, to select these haploids, the first test and the fourth test were employed: invertase content less than 20 units.

This work was carried out until the production of:
5 mutant haploids of mating type a,
5 mutant haploids of mating type α
responding positively to these two tests and for which it has been checked by means of the third test that their adaptation to maltose is retained.

These hybrids were crossed with:
6 haploids derived from slow strains of mating type a,
4 haploids derived from slow strains of mating type α

In this way 50 hybrids were obtained which were tested by means of the first test, the fourth test (invertase content less than 20 units) and the third test as described in example 1.

7 hybrids were selected by means of these screening tests.

After WHITE cultivation, tests in NEW BRUNSWICK type fermenters and tests on the factory scale, 1 hybrid was kept. This hybrid was deposited at the N.C.Y.C. under no. N.C.Y.C. 878. The results obtained with this hybrid in test fermenters of the WHITE type of 3 liters, and in factory tests are reported in Table IV.

TABLE IV

| | In-vert-ase | Test A | | | | | |
|---|---|---|---|---|---|---|---|
| | | 1 hour | Total 2 hours | Test $A_2$ | Test $A_3$ | Test $A_4$ | Test $A_5$ |
| Results of yeasts with 32% dry matter after cultivation in WHITE type fermenters. | 15 | 43 | | 53 | 61 | 28 | |
| Results of fresh yeasts after factory trials. | 5 | 42 + 70 | 112 | 53 | 61 | 44 | 35 |
| | | Test $A_1'$ | $A_2'$ | $A_3'$ | $A_4'$ | $A_5'$ | |
| Results of dry yeasts after factory trials | | 37 + 62 = 99 | 47 | 48 | 35 | 31 | |

EXAMPLE 3

The most interesting strains obtained in examples 1 and 2 were made to sporulate.

The haploids obtained from these noval strains of yeast were crossed with the haploids which were most interesting, that is to say those which led once or, preferably, several times to selected strains.

In this way 110 crossings were carried out which led to 21 hybrids retained after selection according to the first test, the fourth test and the third test, all the three applied as in example 1.

After trials, 2 hybrids were finally retained and deposited at the N.C.Y.C. under nos. N.C.Y.C. 879 and N.C.Y.C. 880.

The results obtained with these two hybrids in WHITE type fermenters of 3 liters in tests are reported in table V below. Their taxonomic characteristics are reported in Table VI. The 5 hybrids obtained within the scope of these examples were all identified as *Saccharomyces Cerevisiae*, by the NCYC, where the hybrids are deposited.

TABLE V

| Results with culture in WHITE type fermenters | Invertase | Test $A_1$ in 1 hour | Test $A_2$ | Test $A_3$ | Test $A_4$ |
|---|---|---|---|---|---|
| N.C.Y.C. 879 | 21 | 48 | 58 | 63 | 28 |
| N.C.Y.C. 880 | 16 | 42 | 54 | 64 | 31 |

These two strains N.C.Y.C. 879 and 880 have properties close to those of strain N.C.Y.C. 878, that is to say they are quicker in all the tests than N.C.Y.C. R30 including Test $A_4$ corresponding to a very sweet dough.

EXAMPLE 4

Throughout the work described in examples 1 to 3, it became recognisable that a certain number of haploids were of particular interest leading to selected hybrids and recognised as having interesting novel properties.

5 of these particularly active haploids were deposited at the N.C.Y.C. These were the haploids:

Ha 1 haploid of mating type a which has received no. N.C.Y.C. 881
Ha 2 haploid of mating type a which has received no. N.C.Y.C. 882
H α 3 haploid of mating type α which has received no. N.C.Y.C. 883
H α 4 haploid of mating type α which received no. N.C.Y.C. 884
H α 5 haploid of mating type α which has received no. N.C.Y.C. 885

These haploids were all obtained by sporulation of *Saccharomyces Cerevisiae* strains.

These haploids cultivated in WHITE type fermenters gave the following results:

| | Invertase content | Test $A_1$ in 1 hour | Test $A_4$ in 1 hour | $\dfrac{\text{Result of Test } A_3}{\text{Result of Test } A_2} \times 100$ |
|---|---|---|---|---|
| Ha$_1$ | 18 | 41 | 29 | 121 |
| Ha$_2$ | 11 | 29 | 17 | 109 |
| Hα$_3$ | 85 | 50 | 13 | 75 |
| Hα$_4$ | | 33 | 15 | 89 |
| Hα$_5$ | 13 | 26 | 35 | 139 |

The two first haploids Ha$_1$ (N.C.Y.C. no. 881) and Ha$_2$ (N.C.Y.C. no. 882) were particularly remarkable:
since they have quick characters, that is to say adaptation to maltose, and osmotolerant, that is to say adaptation to high sugar content,
since they impose the low invertase characteristic after conjugation, that is to say they give systematically diploid strains with low invertase.

They gave interesting results when they were conjugated with haploids derived from quick yeasts as well as when they were conjugated with haploids derived from slow yeasts.

The two haploids Hα$_3$ (N.C.Y.C. no. 883) and Hα$_4$ (N.C.Y.C. no. 884) are interesting and act as examples of haploids derived from non-osmotolerant quick yeasts.

Haploid Hα$_5$ is a good example of a haploid having characters of very good adaptation to sweetened doughs; haploid Hα$_5$ has N.C.Y.C. no. 885.

EXAMPLE 5

Following the work described in examples 1 to 4, the 5 selected strains are made to sporulate, and the haploids obtained from these 5 strains are then crossed with the most performing haploids (i.e. the haploids having led most often to selected hybrids) derived from quick yeast well adapted to maltose and themselves presenting those characteristics in order to obtain new yeast hybrids quicker and even better adapted to maltose than those obtained up till now. The main screening tests retained for this project were the first and third, the other screening tests, and particularly the fourth, being carried out only on the most performing hybrids according to the first and third screening tests.

This hybridization and selection work led to the selection of the hybrid noted in our registers under the number a α1217.

This newly-obtained strain corresponding to the diploid strain obtained by mass-mating was first sent to the National Collection of Yeast Cultures (NCYC) of the Brewing Research Foundation, Lyttel Hall, Nutfield, Redhill, Surrey RH1 4HY, and was given the deposit number NCYC 889.

This new strain corresponding to a purified isolation of the strain obtained directly by mass-mating, was later sent a second time to the NCYC and given the deposit number NCYC 890.

Since the 2 parent strains belong to the species *Saccharomyces Cerevisiae*, this new strain a α1217 also belongs to this same species.

The following results from the different trials carried out on the new strain a α1217 were obtained:

(1) Results obtained from the fresh yeast cultured in White-type fermenters.

|  |  | Test $A_1$ in 1 hr. | Test $A_2$ in 1 hr. | Test $A_3$ in 1 hr. | Test $A_4$ in 1 hr. |
|---|---|---|---|---|---|
| NCYC 889 strain obtained after mass-mating | 1st trial | 19,5 | 52,6 | 60,4 | 55,8 | 22,1 |
|  | 2nd trial |  | 49,1 | 58,2 | 52,9 | 21 |
| Purified strain NCYC 890 |  |  | 52,6 | 61 | 56 | 23,5 |

(2) Results obtained from the fresh yeast cultured in the NBS pilot fermenters (New Brunswick Scientific Co. Inc.)

| Nitrogen on dry matter | Test $A_1$ in 2 hours | Test $A_2$ in 1 hr. | Test $A_3$ in 1 hr. | Test $A_4$ in 1 hr. |
|---|---|---|---|---|
| 7,2 | 134 | 63 | 53 | 24 |

(3) Results from the fresh yeast intended for drying and obtained after factory tests with a culture of 100 m3, giving approximately 25 tons of fresh yeast (non-commercialised yeast).

| | Nitrogen/ on dry matter | Invertase | Test $A_1$ in 1 hr + 1 hr = 2 hrs | Test $A_2$ in 1 hour | Test $A_3$ in 1 hour | Test $A_4$ in 1 hour |
|---|---|---|---|---|---|---|
| Trial 1. | 8,6 | 47 | 63 + 86 = 149 | 67 | 60 | 32 |
| Trial 2. | 8,4 | 43 | 65 + 88 = 154 | 67 | 58 | 33 |
| Trial 3. | 7,9 | 40 | 60 + 83 = 143 | 63 | 57 | 36 |
| Trial 4. | 7,5 | 42 | 58 + 81 = 139 | 62 | 57 | 34 |
| Trial 5. | 7,6 | 40 | 57 + 80 = 137 | 62 | 55 | 32 |

(4) Results from the dried yeast after drying between 95 and 96% of dry matter from the yeast obtained in the below-mentioned factory tests.

| | Test $A_1'$ in 1hr + 1hr = 2hrs | Test $A_2'$ in 1 hour | Test $A_3'$ in 1 hour | Test $A_4'$ in 1 hour | Test $B_1$ in 3 hours |
|---|---|---|---|---|---|
| Trial 1. | 53 + 71 = 124 | 57 | 49 | 27 | |
| Trial 2. | 56 + 74 = 130 | 58 | 50 | 27 | |
| Trial 3. | 52 + 70 = 122 | 53 | 48 | 29 | 1580 |
| Trial 4. | 53 + 70 = 123 | 56 | 49 | 26 | 1670 |
| Trial 5. | 52 + 69 = 121 | 53 | 47 | 26 | |

These results show:

that the yeasts obtained from this strain are as quick and as well adapted to maltose as those yeasts obtained with the best hybrids of quick yeast adapted to maltose, and that in addition, they perform on sweet doughs as well as those obtained with a strain such as the yeast strain NCYC R 30, that the yeasts obtained from the strain a α1217 are particularly stable in drying, that the active dry yeasts obtained from this strain in factory tests are particularly performing since:

in the test $A'_1$, there is a gas release in the first hour amounting to between 45 and 58 ml, and in the 2 hours, a release of between 115 to 130 ml of $CO_2$, and preferably in 1 hour 47 to 58 ml and in 2 hours, 118 to 130 ml, but more preferably 50 to 58 ml in 1 hour and 120 to 130 ml of $CO_2$ in 2 hours, in the test $B_1$, there is a gas release in 3 hours between 1400 and 1800 ml, and preferably between 1450 and 1800 ml, and more preferably between 1500 and 1800 ml, in test $A'_2$, there is a gas release in 1 hour between 50 and 60 ml but preferably between 52 and 60 ml, in test $A'_3$, there is a Gas release in 1 hour between 45 and 54 ml, but preferably between 47 and 54 ml, in test $A'_4$, there is a Gas release in 1 hour between 23 and 30 ml but preferably between 26 and 30 ml.

This new yeast strain a α1217 has a weak performance and acid doughs in tests $A'_5$ and $B_3$, performs may be little better than the quick yeast test hybrids adapted to maltose and is much less active than strains such as NCYC R 30.

TABLE VI

Results of identification tests carried out by the NCYC (National Collection of Yeast Cultures) on the deposited strains
Indication of some particular results on each strain

| Strains tested | Identification result | Size of cells in microns | | | Number of ascospores per ascus | Galactose fermentation | Assimilation | | | | α Methyl-glucoside | Growth in medium without vitamines |
| | | Liquid medium | | Solid medium | | | Trehalose | Melezitose | Inulin | Erythrol | | |
| | | 24 h | 72 h | 72 h | | | | | | | | |
|---|---|---|---|---|---|---|---|---|---|---|---|---|
| NCYC 847 | Saccharomyces Cerevisiae | (3.5–5) × (6.5–9) | (2–5) × (3.5–7.5) | (2–4) × (3–7) | 1 to 4 | + | + latent | + | + | – | + | – |
| NCYC 848 | Saccharomyces Cervisiae | (2.5–4.5) × (4.5–6.5) | (3–4.5) × (4–7) | (2.5–4.5) × (3–8) | 1 to 4 | + | + | + | + | – | + | weakly + |
| NCYC 873 | Saccharomyces Cerevisiae | (3–5) × (5–8) | (2.5–5) × (4–6) | (2–4) × (4–8) | 1 to 4 | + | + | + | + | – | + | – |
| NCYC 879 | Saccharomyces Cerevisiae | (3–5.5) × (4–7) | (2–6) × (3–8.5) | (3–5) × (3–7) | 1 to 4 | + | + | + | + | – | + | ± |
| NCYC 830 | Saccharomyces Cervisiae | | | | 2 to 4 | + | + latent | + | + | – | + | ± |
| NCYC 875 | Saccharomyces Cerevisiae | | (3.6–6) × (4–8) | (1.5–5.5) × (3.5–8) | 1 to 4 | + | + latent | + latent | + | – | + latent | – |
| NCYC 875 | Saccharomyces Cerevisiae | | (3–7) × (4–10) | (3–5) × (4–11) | 1 to 4 | + | + latent | + latent | + | – | ± | – |
| NCYC 877 | Saccharomyces Cerevisiae | | (2–4.5) × (3–6) | (1.5–4.5) × (2.5–9) | 2 | + | + latent | + latent | + | – | + | weak |
| NCYC R 30 | Saccharomyces Cerevisiae | (1.5–8) × (2–7) | (1.5–8) × (2–6) | (2.9–8) × (2.5–7) | 1 to 2 | + 3 weeks | + | + | – | – | + | – |

Remarks:
The nine strains described have been characterised as belonging to the *Saccharomyces Cerevisiae* species. The other characters described in this table are secondary characters, without technological significance. Their reproducibility within the scope of the tests practised (J. LODDER tests) is not always ensured.

The latter examples shows that the screening tests described lead rapidly to defining particularly active haploids, which can impose the desired characters such as for example low invertase content.

These haploids, due to the fact that they have led once or preferably several times to selected diploid strains constitute a genetic starting material which is particularly interesting. It is possible to characterize them by means of conventional tests according to their properties as haploids and in a more advantageous way according to the properties they confer on the diploids after crossing.

Whatever the embodiment adopted there are thus provided:

on the one hand, novel strains of yeasts, on the other hand, fresh and compressed yeasts obtained from these novel strains and constituting novel industrial products, these novel strains as well as the fresh and dried yeasts derived therefrom, having, with respect to those existing hitherto, numerous advantages explained in the description.

The invention relates also, by way of novel industrial products, to the breadmaking products by means of the fresh yeasts and the dry yeasts produced by means of the novel strains of yeasts obtained.

It is self-evident and as is already consequent upon the foregoing, the invention is in no way limited to the embodiments and adaptations which have been more especially envisaged; it encompasses, on the contrary, all modifications.

We claim:

1. The biologically pure man-made yeast strain a α1217, deposited twice at the NCYC under the numbers 889 and 890.

2. Fresh baker's yeast composition obtained from the yeast strain a α1217, of claim 1 and containing dry material of about 28 to 35%.

3. Active dry baker's yeast composition obtained from yeast strain a α1217, of claim 1 and further including an emulsifying agent.

4. An active yeast composition in solid particulate form consisting essentially of an active dry baker's yeast obtained from man-made biologically pure yeast strain and having an emulsifying agent therewith, said composition having a dry matter content of between about 94% and 97% and being characterized by the fact that conjointly:

(a) in test A'$_1$ there is a gas release in 2 hours, of between 120 and 130 ml;

wherein, in said test A'$_1$ 160 mg of dry matter of said dry yeast is rehydrated with 6 ml of distilled water at 38° C. and at the end of 15 minutes of rehydration adding the amount of water, together with 405 mg of NaCl, required to bring the total to 15 ml, to the product resulting from the said fifteen minutes rehydration and then adding the resulting rehydrated yeast/salt/water composition to 20 g of flour at 30° C., thereafter kneading the resulting mixture for 40 seconds to obtain a dough, maintaining said dough at 30° C. in a vessel for 13 minutes after the beginning of said kneading, thereafter hermetically sealing said vessel and measuring the total amount of gas produced, in ml, at 30° C. and 760 mm of Hg, after the expiration of 60 minutes, and then after the expiration of 120 minutes;

(b) in test B$_1$, there is a gas release in 3 hours of between 1500 and 1800 ml;

wherein, in said test B$_1$ 1.6 g of yeast dry matter and 150 ml of water containing 50 g of NaCl per 1.5 liter of water, is added to 250 g of flour, and the mixture is kneaded for 6 minutes under conditions such that the temperature of the resulting dough at the end of said kneading is 27° C., that dough is then placed in the chamber of a Chopin zymotachygraph, and exactly 6 minutes after said kneading, said chamber is placed under pressure and maintained at 27° C., and recording the total gas release in ml on a graph at the expiration of 1 hour, and also after the expiration of 3 hours;

(c) in test $A'_2$, there is a gas release in 1 hour of between 52 and 60 ml;

wherein, in said test $A'_2$ the procedure of said test $A'_1$ is followed except that there is added to said flour 100 mg of saccharose, and the total amount of gas produced is measured after the expiration of 60 minutes;

(d) in test $A'_3$, there is a gas release in 1 hour, of between 47 and 54 ml;

wherein, in said test $A'_3$ the procedure of said test $A'_1$ is followed except that there is added to said flour 2 g of saccharose and the total amount of gas produced is measured after 60 minutes;

(e) in test $A'_4$, there is a gas release in 1 hour, of between 26 and 30 ml;

wherein, in said test $A'_4$ the procedure of said test $A'_1$ is followed except that there is added to said flour 5.5 g of saccharose, and the total amount of gas produced is measured after 60 minutes.

* * * * *